US012158573B2

(12) United States Patent
Essig et al.

(10) Patent No.: US 12,158,573 B2
(45) Date of Patent: Dec. 3, 2024

(54) CONTACTLESS VISUALIZATION SYSTEM FOR A SURGICAL MICROSCOPE FOR EYE SURGERY

(71) Applicant: Carl Zeiss Meditec AG, Jena (DE)

(72) Inventors: Jonathan Essig, Aalen (DE); Christian Beder, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 18/422,817

(22) Filed: Jan. 25, 2024

(65) Prior Publication Data

US 2024/0168279 A1    May 23, 2024

Related U.S. Application Data

(63) Continuation of application No. PCT/EP2022/068719, filed on Jul. 6, 2022.

(30) Foreign Application Priority Data

Jul. 26, 2021   (DE) ..................... 10 2021 119 297.8

(51) Int. Cl.
  *G02B 25/00*  (2006.01)
  *G02C 3/04*  (2006.01)
(52) U.S. Cl.
  CPC ............. *G02B 25/008* (2013.01); *G02C 3/04* (2013.01)
(58) Field of Classification Search
  CPC .. G02B 25/008; G02B 7/026; G02B 27/0006; G02B 21/0012; G02C 3/04; A61B 3/125;

(Continued)

(56) References Cited

U.S. PATENT DOCUMENTS 5,706,073 A    1/1998  Volk
6,019,472 A    2/2000  Koester et al.
(Continued)

FOREIGN PATENT DOCUMENTS

CN         107405069 A    11/2017
DE    10 2008 022 211 B3    2/2010
(Continued)

OTHER PUBLICATIONS

English translation and Written Opinion of the International Searching Authority dated Oct. 28, 2022 for international application PCT/EP2022/068719 on which this application is based.

(Continued)

*Primary Examiner* — Tuyen Tra
(74) *Attorney, Agent, or Firm* — Walter Ottesen, P.A.

(57) ABSTRACT

A contactless visualization system is for a surgical microscope for eye surgery. The system includes an ophthalmic loupe positionable in front of a patient's eye and for supplying a real and vertically and laterally inverted image of an eye fundus of the patient's eye in an intermediate image plane observable by the surgical microscope. The ophthalmic loupe includes a first and a second lens element. In a state positioned in front of the patient's eye, the first lens element is closer to the patient's eye than the second lens element. A wall extends from the first to the second lens element. The wall has a free end in a form of a mount in which the second lens element is held. The mount includes at least one cutout in which an edge of the second lens element is exposed in order to give a surgeon operating space.

16 Claims, 4 Drawing Sheets

(58) Field of Classification Search
CPC ... A61B 2090/3616; A61B 3/13; A61B 90/20; A61B 3/12; A61F 9/00736
See application file for complete search history.

(56) References Cited

U.S. PATENT DOCUMENTS

| | | | |
|---|---|---|---|
| 7,244,026 B1* | 7/2007 | Ross, III | G02B 7/025 351/219 |
| 7,338,170 B2* | 3/2008 | Cech | A61B 3/12 351/218 |
| 7,946,706 B2* | 5/2011 | Cech | G02B 7/021 623/4.1 |
| 9,526,428 B2* | 12/2016 | Denner | A61B 3/10 |
| 10,765,315 B2 | 9/2020 | Doushkina et al. | |
| 2003/0103191 A1 | 6/2003 | Staurenghi et al. | |
| 2008/0084540 A1 | 4/2008 | Gaida | |
| 2012/0099077 A1 | 4/2012 | Abt | |
| 2016/0195690 A1 | 7/2016 | Reimer et al. | |
| 2016/0317032 A1 | 11/2016 | Smith et al. | |
| 2019/0369353 A1 | 12/2019 | Franklin et al. | |
| 2021/0259880 A1 | 8/2021 | Newton et al. | |

FOREIGN PATENT DOCUMENTS

| | | |
|---|---|---|
| EP | 1 308 124 A2 | 5/2003 |
| EP | 2 613 688 B1 | 4/2015 |
| JP | H7-5353 A | 1/1995 |
| JP | 2003-29113 A | 1/2003 |
| JP | 2009-222740 A | 10/2009 |
| WO | 99/20171 A1 | 4/1999 |
| WO | 2015/001200 A1 | 1/2015 |
| WO | 2021/138641 A1 | 7/2021 |

OTHER PUBLICATIONS

English translation and International Preliminary Report on Patentability of the European Patent Office dated Jun. 13, 2023 for international application PCT/EP2022/068719 on which this application is based.

International Search Report of the European Patent Office dated Oct. 28, 2022 for international application PCT/EP2022/068719 on which this application is based.

English translation of First Office Action of the Chinese Patent Office dated Aug. 2, 2024 for corresponding Chinese patent application 202280051312.8.

* cited by examiner

CONTACTLESS VISUALIZATION SYSTEM FOR A SURGICAL MICROSCOPE FOR EYE SURGERY

CROSS-REFERENCE TO RELATED APPLICATIONS

This application is a continuation application of international patent application PCT/EP2022/068719, filed Jul. 6, 2022, designating the United States and claiming priority from German application 10 2021 119 297.8, filed Jul. 26, 2021, and the entire content of both applications is incorporated herein by reference.

TECHNICAL FIELD

The present disclosure relates to a contactless visualization system for a surgical microscope for eye surgery.

BACKGROUND

So-called contactless visualization systems are readily used for ophthalmic surgery on the posterior section of the eye, and these have started to take over from the previous visualization via a contact glass placed on the patient's eye. These systems operate with what are known as ophthalmic loupes, which are placed just above the patient's eye and supply a real (albeit laterally and vertically inverted) image of the eye fundus in an intermediate image plane, which in turn can then be observed using a surgical microscope.

As a result of placing the ophthalmic loupe close to the patient's eye, the operating space of the surgeon is restricted. This is a difficulty particularly in the case of ophthalmic loupes with multiple lens elements (for example including two lens elements), since the mount needed here for the plurality of lens elements further restricts the operating space for the surgeon. This leads to an unwanted impairment of the surgical procedure.

U.S. Pat. No. 10,765,315 B2 describes a contactless visualization system for a surgical microscope for eye surgery. WO 99/20171 A1 describes an indirect visualization system including a contact lens element facing the eye and a further lens element spaced apart therefrom.

SUMMARY

Against this background, it is an object of the disclosure to provide a contactless visualization system of the type set forth at the outset, in such a way that the aforementioned difficulties can be overcome as completely as possible.

The aforementioned object is, for example, achieved via a contactless visualization system for a surgical microscope for eye surgery. The contactless visualization system includes: an ophthalmic loupe configured to be positionable in front of a patient's eye and to supply a real and vertically and laterally inverted image of an eye fundus of the patient's eye in an intermediate image plane that is observable by the surgical microscope; the ophthalmic loupe including a first lens element and a second lens element, wherein, in a state positioned in front of the patient's eye, the first lens element is closer to the patient's eye than the second lens element; a wall extending from the first lens element to the second lens element, the wall having a free end in a form of a mount in which the second lens element is held; and, the mount including at least one cutout in which an edge of the second lens element is exposed in order to give a surgeon operating space.

The aforementioned object is, for example, also achieved via a surgical microscope for eye surgery. The surgical microscope includes: a contactless visualization system having an ophthalmic loupe and a wall; the ophthalmic loupe configured to be positionable in front of a patient's eye and to supply a real and vertically and laterally inverted image of an eye fundus of the patient's eye in an intermediate image plane that is observable by the surgical microscope; the ophthalmic loupe including a first lens element and a second lens element, wherein, in a state positioned in front of the patient's eye, the first lens element is closer to the patient's eye than the second lens element; the wall extending from the first lens element to the second lens element, the wall having a free end in a form of a mount in which the second lens element is held; and, the mount including at least one cutout in which an edge of the second lens element is exposed in order to give a surgeon operating space.

Since the wall serves as a mount for the second lens element at the same time, it must have certain mechanical minimum dimensions and thicknesses for reasons of stability. The necessary stability is retained according to the disclosure since only the at least one cutout, in which the edge of the second lens element is exposed, is provided in order to give a surgeon more operating space.

The cutout may extend in the wall in the direction of the first lens element from the free end, with the cutout preferably not extending to the upper side of the first lens element but ending therebefore. Consequently, a certain height of wall is still provided even in the region of the cutout; this is advantageous for reasons of stability.

The cutout may taper in the direction of the first lens element.

This may relate to exactly one cutout, in which the edge of the second lens element is exposed, or to a plurality of cutouts, in which the edge of the second lens element is exposed. The wall can be embodied such that no further opening or cutout is provided. However, it is alternatively by all means possible that one or more further openings and/or cutouts are still formed in the wall.

Since the wall serves as a mount for the second lens element at the same time, it must have certain mechanical minimum dimensions and thicknesses for reasons of stability. It can be preferable for the wall to be formed throughout in the circumferential direction. That is, the cutout(s) and optionally the further opening(s) are preferably arranged such that the wall is not interrupted or completely interrupted in the circumferential direction. Therefore, the wall is preferably formed such that, in each position in the circumferential direction, the wall includes at least one portion that extends in the direction from the first to the second lens element. Expressed differently, the wall can be embodied such that the wall is fully closed in the circumferential direction or that at least one imaginary, closed curve runs on the wall in the circumferential direction.

In particular, provision is made of two cutouts which, in the circumferential direction, are preferably spaced apart by 80° to 140°, in particular by 90° to 130°, and particularly preferably by 120°. This spacing preferably relates to the center of the respective cutout in the circumferential direction. In the circumferential direction, the width of the cutout at the free end can be 20° to 70°, in particular 30° to 60° or 30° to 50°, and particularly preferably 35° to 45°. Thus, the width can be 40°, for example.

The ophthalmic loupe may include a holder connector, via which the ophthalmic loupe is mechanically connectable to the surgical microscope, wherein the holder connector is connected to the mount at a connection site and the at least one cutout is spaced apart from the connection site by 90° to 150° in the circumferential direction (preferably in relation to the center of the cutout in the circumferential direction and the center of the connection site in the circumferential direction).

Furthermore, at least one passage opening can be formed in the wall. This at least one passage opening serves to be able to remove liquid possibly present in the intermediate space between the two lens elements. This may relate to exactly one passage opening for removing liquid or to a plurality of passage openings for removing liquid.

This firstly guarantees the required mechanical stability and secondly ensures a removal of liquid.

In the circumferential direction, the at least one passage opening may include a width of 20° to 70°, in particular of 30° to 60° or 30° to 50°, and particularly preferably of 35° to 45°. For example, the width can be 40°.

In particular, the wall can be formed as a one-piece part together with the first lens element. This is particularly preferably an injection-molded part. This provides the option of embodying the ophthalmic loupe as a disposable product or disposable article and, at the same time, ensuring the necessary optical quality. By way of the mount, it is possible to ensure that the second lens element is positioned at the optically specified position relative to the first lens element. The one-piece embodiment of the wall with the first lens element is preferably realized as a cohesive connection. However, a realization via an interlocking connection is also possible.

In particular, the second lens element can be arranged concentrically with the first lens element.

The at least one passage opening is preferably formed closer to the first lens element than the second lens element. In particular, the at least one passage opening can be formed such that its lower edge directly bounds on the boundary surface of the first lens element facing the second lens element. The lower edge bounding the boundary surface of the first lens element in this case is preferably of a form where no depression is provided as a result. For example, the lower edge may extend perpendicularly to the optical axis of the first lens element.

A plurality of passage openings may be formed in the wall and spaced apart from one another in the circumferential direction in the case of the visualization system according to the disclosure. Hence, the at least one passage opening may include a plurality of passage openings. In this case, this may relate to two, three, four, five, or more passage openings.

By way of example, three passage openings may be provided, which are each spaced apart from one another by 120° in the circumferential direction. This spacing preferably relates to the center of the respective passage opening in the circumferential direction.

The first lens element and/or the wall may be made of plastic. In addition to the first lens element, the second lens element may also be made of plastic. The second lens element may include a holder connector, which can be formed integrally with the second lens element. In particular, the holder connector may be produced together with the second lens element by way of a two-component injection-molding method. The integral form of the second lens element with the holder connector is preferably realized as an interlocking connection. However, a realization via an interlocking connection is also possible.

The mount can be in the form of a snap-in closure, a clamping connection, or an elastic clamping holder. To this end, the mount may include a plurality of elastic clamping fingers (for example three such clamping fingers spaced apart from one another in the circumferential direction, for example by 120° in relation to the center of the respective clamping finger in the circumferential direction), which for example each include a clamping groove. The second lens element may have corresponding mount regions which project into the clamping grooves. Further, the mount may include corresponding mount regions, which include stop faces for the second lens element or for the mount regions of the second lens element.

However, any other type of hold via the mount is also possible, for example a screw-in connection, a bayonet connection, et cetera.

It can be preferable for the at least one cutout and the at least one passage opening to be arranged offset from one another in the circumferential direction. In particular, the at least one cutout and the at least one passage opening can be arranged such that they are in each case spaced apart from one another in the circumferential direction. For example, the distance can be 60° (in relation to the center of the respective cutout in the circumferential direction and the center of the respective passage opening in the circumferential direction).

Further, the first lens element and the wall may jointly include an n-fold rotational symmetry if n passage openings and/or n cutouts are provided, where n is an integer $\geq 1$ and $\leq 6$. Particularly preferably, n=3.

The contactless visualization system may further include an ophthalmic loupe support, to which the ophthalmic loupe is mechanically connected. Via the ophthalmic loupe support, the ophthalmic loupe can be positioned in the imaging beam path of the surgical microscope and moved out of the imaging beam path. To this end, the ophthalmic loupe support may further be mechanically connected to the surgical microscope. Further, the ophthalmic loupe support may be embodied such that a rotational movement of the ophthalmic loupe about the optical axis of the surgical microscope is possible. Hence, a user can bring the ophthalmic loupe into a rotational position that they desire and they consider advantageous, for example when using the ophthalmic loupe.

Moreover, the mechanical connection between the ophthalmic loupe and the ophthalmic loupe support can be a detachable connection, with the result that the ophthalmic loupe is interchangeable. This is particularly advantageous if the ophthalmic loupe is in the form of a disposable article.

The surgical microscope according to the disclosure for eye surgery can be in the form of a 3-D surgical microscope in particular.

BRIEF DESCRIPTION OF DRAWINGS

The invention will now be described with reference to the drawings wherein.

DETAILED DESCRIPTION

Figure 1:
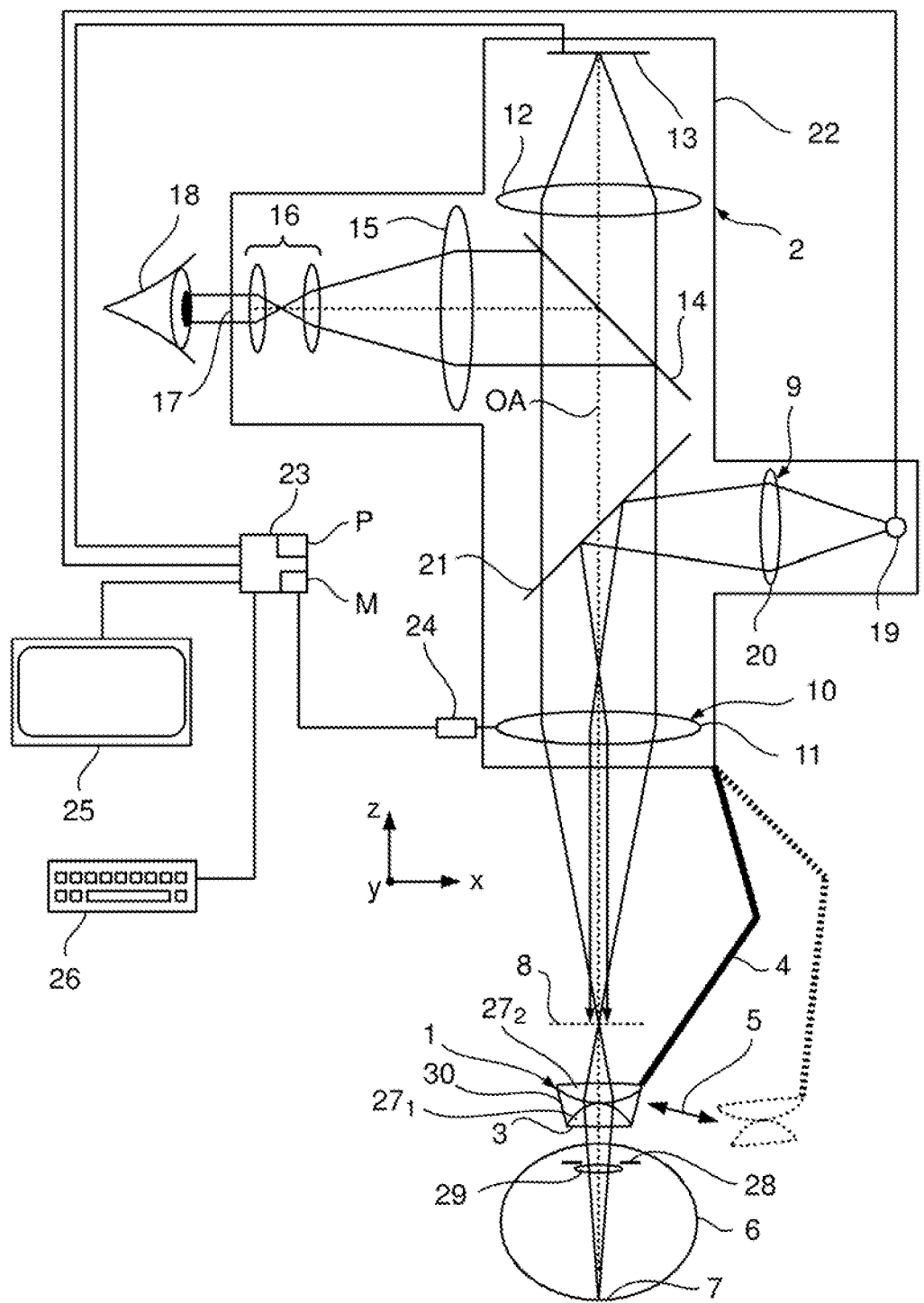
FIG. 1 shows a schematic view of an embodiment of the contactless visualization system 1 in conjunction with a surgical microscope 2.

In the case of the embodiment of a contactless visualization system 1 shown in FIG. 1, the latter is shown together with a surgical microscope 2 for eye surgery. The contactless visualization system 1 includes an ophthalmic loupe 3 and an ophthalmic loupe support 4, via which the ophthalmic loupe 3 can be pushed into (or positioned in) an imaging beam path of the surgical microscope 2 and pushed out of (or removed from) the imaging beam path, as depicted schematically by the double-headed arrow 5 in FIG. 1. The position of the ophthalmic loupe 3 outside of the imaging beam path is depicted using dashed lines in FIG. 1.

As may be further gathered from FIG. 1, the ophthalmic loupe 3 can be placed just above a patient's eye 6 via the ophthalmic loupe support 4, with the result that a real and vertically and laterally inverted image of the eye fundus 7 of the patient's eye 6 is imaged in an intermediate image plane 8. This real and vertically and laterally inverted image of the eye fundus 7 is then observed using the surgical microscope 2.

The surgical microscope 2 may include an illumination unit 9 for illuminating the patient's eye 6 (for example, the eye fundus 7 in this case) and an imaging optical unit 10 for the magnified imaging of the illuminated patient's eye 6 and, in this case, for magnified imaging of the image in the intermediate image plane 8 as well. The patient's eye 6 with the eye pupil 28 and the crystalline lens 29 is only depicted schematically here.

The imaging optical unit 10 depicted schematically in FIG. 1 includes a lens 11 and a first tube optical unit 12 for imaging the illuminated region of the patient's eye 6 on an image sensor 13. Moreover, the imaging optical unit 10 includes a first beam splitter 14, which is arranged between the lens 11 and the first tube optical unit 12, and a second tube optical unit 15 disposed downstream of the first beam splitter 14 and an eyepiece optical unit 16 disposed downstream of the second tube optical unit 15 such that an optical eyepiece 17 is provided, as indicated by the schematically depicted eye 18 of a user.

The illumination unit 9 includes a light source 19, a collector optical unit 20 disposed downstream of the light source 19, a second beam splitter 21 that is arranged between the lens 11 and the first tube optical unit 12, and the lens 11. The light from the light source 19 is focused via the collector optical unit 20 and input coupled into the beam path between the second beam splitter 21 and the lens 11 via the second beam splitter 21 in such a way that the region of the patient's eye 6 to be illuminated is illuminated as uniformly as possible, as indicated in FIG. 1 with a schematic beam profile up to the intermediate image plane 8. By way of example, the light source 19 can be in the form of a halogen lamp, a xenon discharge lamp, an LED, or a laser.

The elements of the surgical microscope 2 described up until this point are arranged within a housing 22, as depicted schematically in FIG. 1. The ophthalmic loupe support 4 is mechanically connected to the housing 22, wherein, in addition to the sliding in and out of the ophthalmic loupe 3 indicated schematically in FIG. 1, a turret mechanism may also be formed on the ophthalmic loupe support 4, with the result that a rotation of the ophthalmic loupe 3 about the z-axis and, in this case, about the optical axis OA of the imaging beam path of the surgical microscope 2 is also possible.

Further, the surgical microscope 2 includes a controller 23, which includes a processor P and a memory M and is connected, for example, to the light source 19, the image sensor 13, and a z-drive 24, via which the lens 11 can be moved in the z-direction for focusing.

Further, an electronic visual display 25 and an input unit 26 may be connected to the controller 23, as depicted schematically in FIG. 1. In this case, the input unit 26 is depicted only schematically as a keyboard. Other types of input units, for example foot switches and the like, are also possible.

In this case, the ophthalmic loupe 3 includes exactly one first plastic lens element $27_1$ with a first and a second boundary surface 35, 36 and a second plastic lens element $27_2$ with a first and a second boundary surface 37, 38, with a wall 30 extending in the direction of the second lens element $27_2$ being formed in one piece with the first plastic lens element $27_1$. The free end 31 of the wall 30 serves as a mount 32, as is identifiable in conjunction with FIGS. 2 to 5 in particular. The boundary surfaces 35-38 preferably have a curved form, with at least one of the boundary surfaces 35-38 being aspherically curved. The remaining boundary surface or surfaces is/are preferably spherically curved.

The mount 32 includes a first, a second, and a third mount portion 40, 41, and 42, which are in each case spaced apart from one another by 120° in the circumferential direction. Each mount portion 40-42 includes a first and a second stop region $40_1$, $40_2$; $41_1$, $41_2$ and also $42_1$ and $42_2$, between which an elastic clamping finger 43, 44, 45 with a clamping groove $43_1$, $44_1$, $45_1$ is arranged in each case.

The second lens element $27_2$ includes three mount regions $49_1$-$49_3$ (identifiable in FIGS. 2 and 3 in particular), which are clamped in the clamping grooves $43_1$, $44_1$ and $45_1$ of the elastic clamping fingers 43-45 and are in contact with the stop regions $40_1$-$40_3$ such that the second lens element $27_2$ is held concentrically with the first lens element $27_1$. This type of clamping connection between the mount 32 and the second lens element $27_2$ can also be referred to as a snap-in connection.

The second lens element $27_2$ additionally includes a holder connector 55, via which a detachable connection to the ophthalmic loupe support 4 is possible.

Since the wall 30 serves as a mount 32 for the second lens element $27_2$ at the same time, it must have certain mechanical minimum dimensions and thicknesses for reasons of stability. This leads to the wall 30 having a substantially closed embodiment, with the result that liquid can collect between the two lens elements $27_1$ and $27_2$, but is unable to drain again. This would lead to the optical imaging quality suffering greatly, whereby only partly focused imaging or no further focused imaging at all is possible under certain circumstances.

Therefore, in its lower region (and hence near the first lens element $27_1$), the wall 30 here includes three passage openings 46, 47, and 48 which are spaced apart from one another in the circumferential direction and are arranged here with an offset of 120° from one another in the circumferential direction. The width of each passage opening 46-48 in the circumferential direction can be 40°, for example. On account of these passage openings 46-48, it is possible that either the unwanted liquid drains by itself and/or the user (for example the surgeon) removes the liquid when necessary. To this end, for example, an appropriate, liquid-absorbing tool (for example, a swab) can be held against or in the passage openings 46-48.

Hence, unwanted liquid can easily be removed from the intermediate space between the two lens elements $27_1$ and $27_2$, and it is possible to ensure the desired optical imaging quality for good.

Figure 3:
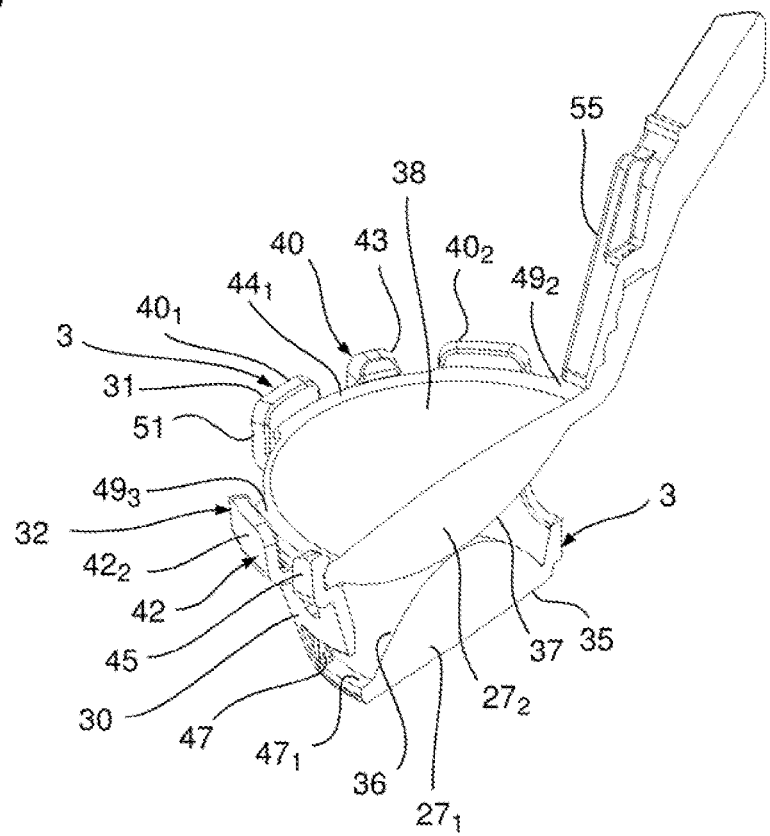
FIG. 3 shows a perspective sectional illustration of the ophthalmic loupe 3 from FIG. 2.

As evident in FIG. 3 in particular, the passage openings 46-48 are preferably of a form where their lower edge $46_1$, $47_1$, $48_1$ borders the upper boundary surface 36 of the first lens element $27_1$. The upper boundary surface 36 is the boundary surface of the first lens element $27_1$ facing the second lens element $27_2$. Preferably, the lower edge $46_1$, $47_1$, $48_1$ of the passage opening 46-48 is of a form where no depression is generated between the lower edge $46_1$, $47_1$, $48_1$ of the passage opening 46-48 and the upper boundary surface 36. For example, in the case present here, the lower edge $461$, $47_1$, $48_1$ is of a form where it extends substantially perpendicularly to the optical axis of the first lens element $27_1$.

There is the further problem that, on account of the mount 32, more space is taken up laterally next to the second lens element $27_2$ in comparison with previous, virtually edgeless ophthalmic loupes with only a single lens element. This restricts the working space of the surgeon. In order to be able to provide the desired hold of the second lens element $27_1$ via the mount 32, certain mechanical minimum dimensions and thicknesses of the wall 30 are mandatory for reasons of stability. However, it was identified that, to this end, it is not necessary for the mount 32 to hold the entire edge of the second lens element $27_2$. Therefore, the wall 30 is embodied in such a way here that two cutouts 50 and 51 are provided, in which the edge of the second lens element $27_2$ is exposed. The two cutouts 50 and 51 are spaced apart from one another in the circumferential direction, for example by 120°. Further, a third cutout 52 is also provided in order to provide sufficient space for the holder connector 55 in the region of the mount 32.

However, the cutouts 50 and 51 are provided for the user or surgeon. If the position of the holder connector 55 is denoted 12 o'clock, then the first and second cutouts 50 and 51 are preferably provided at the positions of 4 o'clock and 8 o'clock, since it is there that the hands of the surgeon come to rest.

Figure 2:
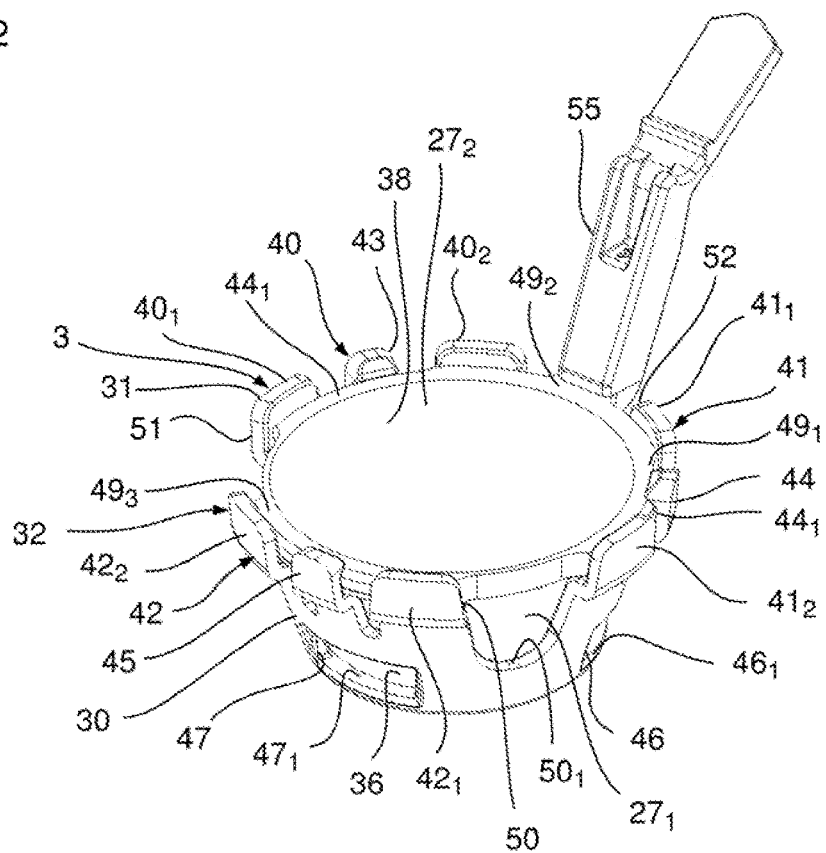
FIG. 2 shows a perspective illustration of the ophthalmic loupe 3 from FIG. 1.
Figure 4:
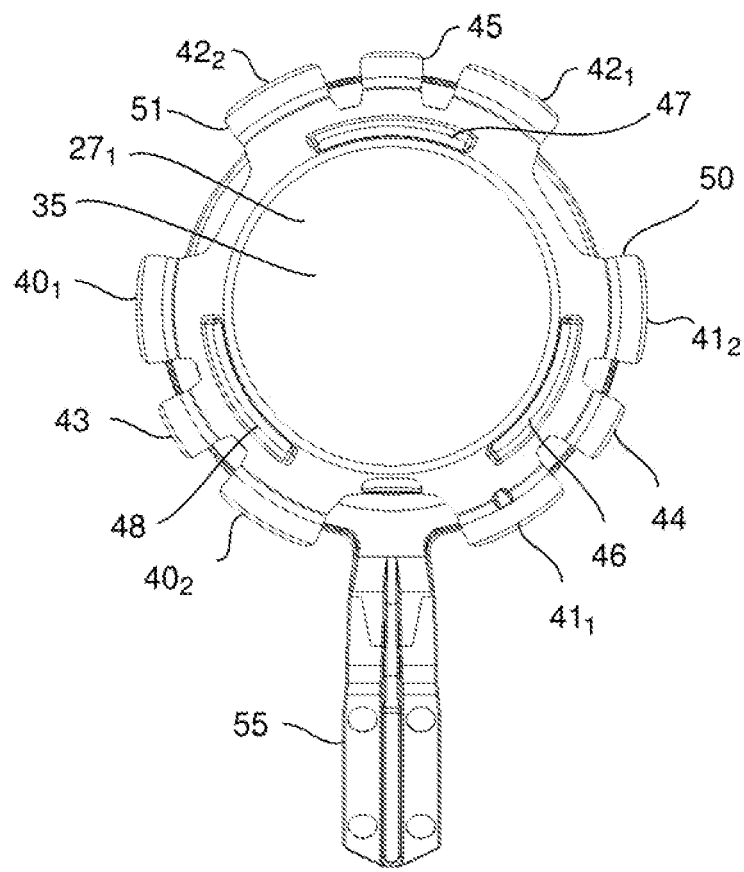
FIG. 4 shows a view from below of the first lens element $27_1$ of the ophthalmic loupe 3 from FIG. 1.

As evident in FIGS. 2 to 4 in particular, the first and second cutouts 50 and 51 extend from the free end 31 in the direction of the first lens element $27_1$. In the embodiment described here, the cutouts 50-51 do not extend up to the upper boundary 36 of the first lens element $27_1$ but end therebefore, in order to still provide a certain height of the wall 30 in the region of the cutouts 50 and 51 for reasons of stability. The lower edge $50_1$, $50_2$ of the cutouts 50 and 51 is thus located above the lower edge $46_1$, $47_1$, $48_1$ of the passage openings 46-48. The same applies to the lower edge 521 of the cutout 52. At the free end 31 of the wall 30, each of the two cutouts 50 and 51 includes an extent in the circumferential direction of 40°, for example. The distance between the cutouts 50 and 51 in the circumferential direction, for example 120° in this case, relates to the centers of the cutouts 50, 51 at the free end 31 of the wall 30. In the circumferential direction, the cutout 52 is spaced apart from the two cutouts 50 and 51 by 120°.

Figure 5:
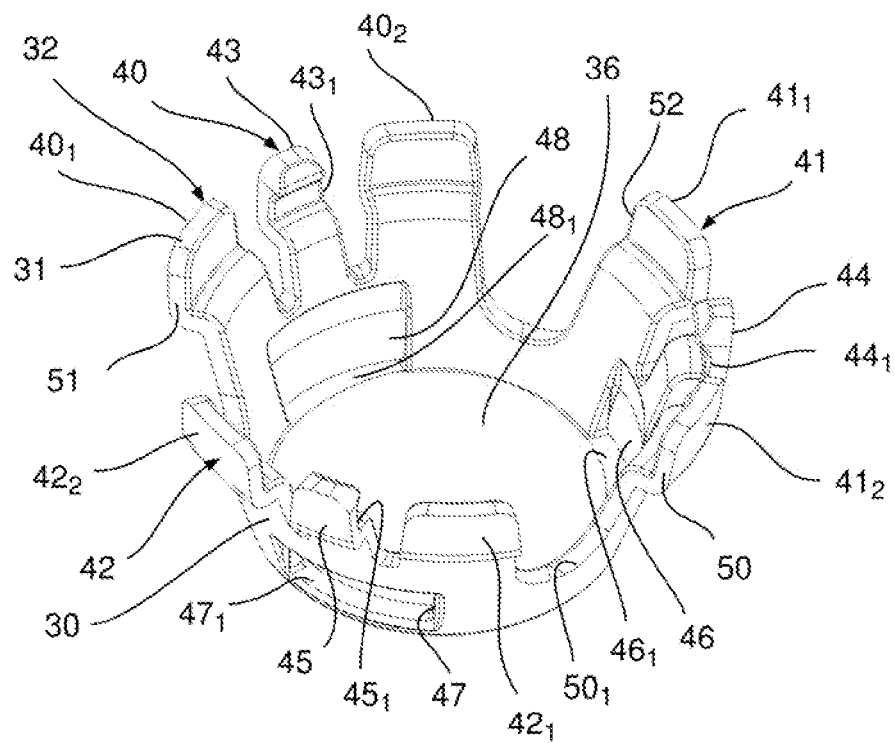
FIG. 5 shows a perspective illustration of the first lens element $27_1$ with the wall 30 of the ophthalmic loupe 3 from FIG. 1.

As may be gathered from FIGS. 2, 3, and 5 in particular, the extent (or width) of the cutout 50, 51 in the circumferential direction tapers in a direction from the second lens element $27_2$ to the first lens element $27_1$. It could also be said that the width of the cutouts 50, 51 reduces in the direction of the lower edge $50_1$, 502, or that the cutouts 50, 51 taper.

As may be gathered from FIGS. 2 to 5, the passage openings 46-48 and the cutouts 50-52 are arranged in such a way in the circumferential direction that a cutout 50-52 and a passage opening 46-48 is provided alternately in each case. For example, in the circumferential direction, these are offset from one another by 60° in each case. In this way, a desired minimum height and hence a certain minimum stability can be provided at each location of the wall 30.

In particular, the wall 30 is thus formed throughout in the circumferential direction. Therefore, the wall 30 is not interrupted in the circumferential direction. Hence, there is no position in the circumferential direction at which, in the direction from the first to the second lens element $27_1$, $27_2$, a part of the wall does not extend over at least a certain section. Expressed differently, a closed curve running on the wall in the circumferential direction can be imagined. Hence, there is always a closed path in the circumferential direction.

In this case, the first lens element $27_1$ (with the wall 30) has such a symmetrical form that a rotation of the first lens element $27_1$ (with the wall 30) through 120° about the optical axis of the first lens element $27_1$ (with the wall 30) maps onto itself. Hence, there is a 3-fold rotational symmetry present.

The ophthalmic loupe 3 can in particular be embodied such that it is detachably connected to the ophthalmic loupe support 4. In this case, it is for example preferable for the ophthalmic loupe 3 to be embodied as a disposable article, and thus be usable precisely once. Following its use, the ophthalmic loupe 3 is disposed, as a result of which there are in particular no problems with otherwise required cleaning and disinfection of the ophthalmic loupe 3. In this case, the ophthalmic loupe 3 is preferably made of plastic. In particular, it can be a plastic molded part.

Figure 6:
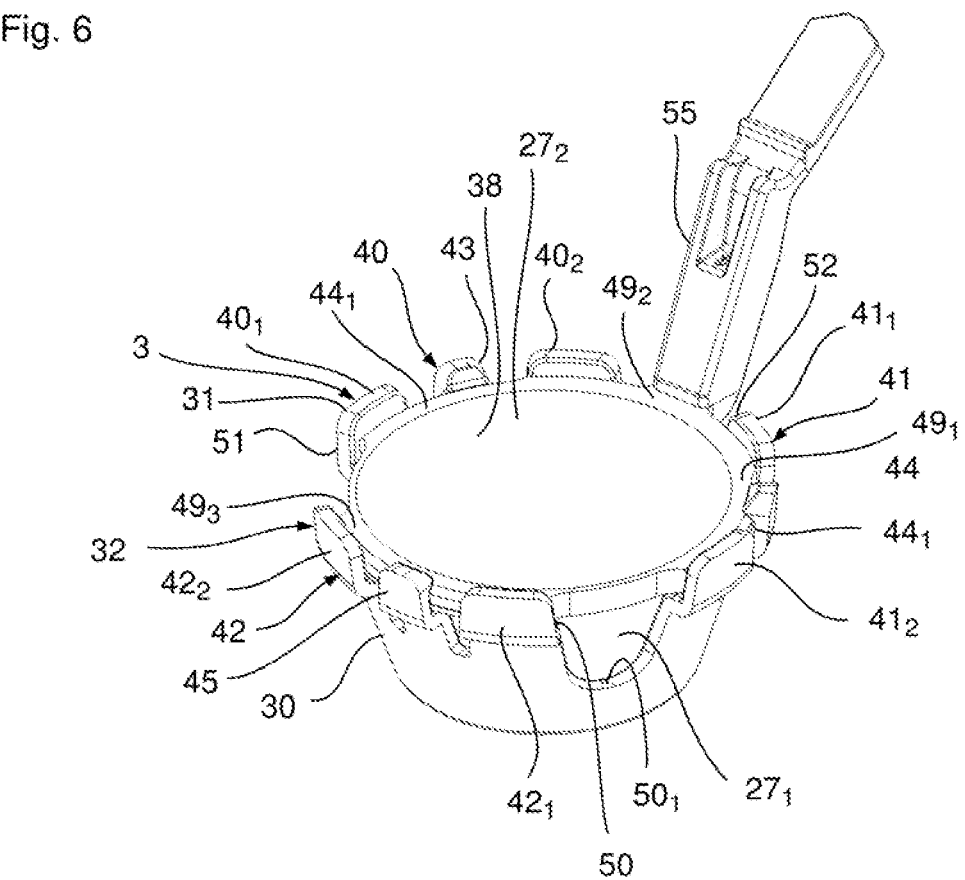
FIG. 6 shows a perspective illustration of a further embodiment of the ophthalmic loupe 3 from FIG. 1; and, FIG. 7 shows a perspective illustration of a further embodiment of the ophthalmic loupe 3 from FIG. 1.

FIG. 6 shows a further embodiment of a contactless visualization system 1, which can be used together with the surgical microscope 2 according to FIG. 1. Only the cutouts 50, 51, and 52 are provided in this embodiment. However, the wall 30 does not contain any passage openings, as are present in the embodiment of FIGS. 2 to 5.

An advantage obtained by the embodiment according to FIG. 6 is that sufficient operating space is provided for the user or surgeon even in the region of the second lens element $27_2$ since the cutouts 50 and 51 are provided. Consequently, the embodiment according to FIG. 6 only differs from the embodiment according to FIGS. 2 to 5 in that no passage openings are provided. All other features and configurations of the embodiments of FIGS. 2 to 5 are present, however.

Figure 7:
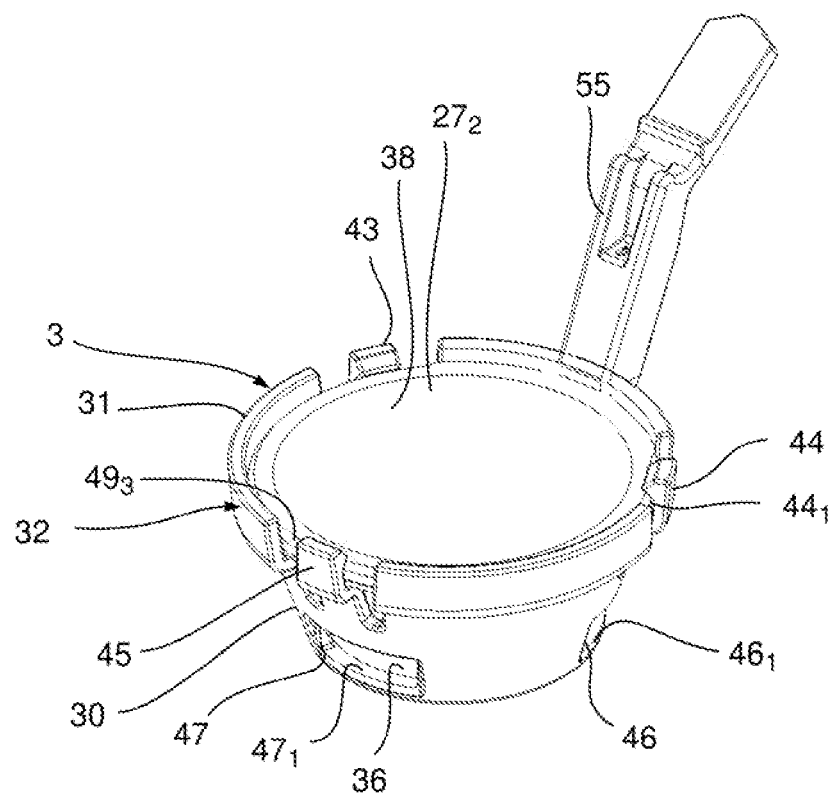

FIG. 7 shows a further embodiment of a contactless visualization system 1, which can be used together with the surgical microscope 2 according to FIG. 1. In this embodiment, the ophthalmic loupe 3 only includes the passage openings 46-48. However, the cutouts 50-52 are not provided. Otherwise, all features of the embodiment according to FIGS. 2 to 5 are implemented in the same way. Consequently, an advantage of the embodiment according to FIG. 7 is that liquid which may collect in the space between the two lens elements $27_1$ and $27_2$ either drains by itself and/or can be removed by the user when necessary.

It is understood that the foregoing description is that of the preferred embodiments of the invention and that various changes and modifications may be made thereto without departing from the spirit and scope of the invention as defined in the appended claims.

The invention claimed is:

1. A contactless visualization system for a surgical microscope for eye surgery, the contactless visualization system comprising:

an ophthalmic loupe configured to be positionable in front of a patient's eye and to supply a real and vertically and laterally inverted image of an eye fundus of the patient's eye in an intermediate image plane that is observable by the surgical microscope;

said ophthalmic loupe including a first lens element and a second lens element, wherein, in a state positioned in front of the patient's eye, said first lens element is closer to the patient's eye than said second lens element;

a wall extending from said first lens element to said second lens element, said wall having a free end in a form of a mount in which said second lens element is held; and, said mount including at least one cutout in which an edge of said second lens element is exposed in order to give a surgeon operating space.

2. The contactless visualization system of claim 1, wherein said wall is uninterrupted in a circumferential direction.

3. The contactless visualization system of claim 1, wherein:

said ophthalmic loupe includes a holder connector via which said ophthalmic loupe is mechanically connectable to the surgical microscope; and, said holder connector is connected to said mount at a connection site and a center of said at least one cutout is spaced apart from a center of said connection site in a circumferential direction by 90° to 150° in a circumferential direction.

4. The contactless visualization system of claim 1, wherein said at least one cutout includes two cutouts which are formed in said mount and said two cutouts each have centers which are spaced apart from one another by 60° to 180° in a circumferential direction.

5. The contactless visualization system of claim 1, wherein at said free end, said at least one cutout extends through 20° to 70° in a circumferential direction.

6. The contactless visualization system of claim 1, wherein said at least one cutout extends in said wall from said free end in a direction of said first lens element such that said at least one cutout ends above said first lens element and a predetermined height of the wall is still present below said at least one cutout.

7. The contactless visualization system of claim 1, wherein said wall is formed as a one-piece part together with said first lens element.

8. The contactless visualization system of claim 1, wherein said wall defines at least one passage opening in order to be able to remove liquid possibly present in an intermediate space between said first lens element and said second lens element.

9. The contactless visualization system of claim 8, wherein said at least one passage opening is formed closer to said first lens element than said second lens element.

10. The contactless visualization system of claim 8, wherein a plurality of passage openings are formed in said wall and mutually spaced apart in a circumferential direction.

11. The contactless visualization system of claim 8, wherein said first lens element includes a boundary surface facing said second lens element and has a curved form; and, said at least one passage opening includes a lower edge which borders on said boundary surface of said first lens element.

12. The contactless visualization system of claim 8, wherein said at least one passage opening is offset with respect to at least one cutout arranged in a circumferential direction.

13. The contactless visualization system of claim 1, wherein said mount is an elastic clamping holder.

14. The contactless visualization system of claim 1 further comprising:

an ophthalmic loupe support;

said ophthalmic loupe being mechanically connected to said ophthalmic loupe support; and, said ophthalmic loupe support being configured to position said ophthalmic loupe in front of the patient's eye.

15. The contactless visualization system of claim 14, wherein said ophthalmic loupe is detachably connected to said ophthalmic loupe support.

16. A surgical microscope for eye surgery, the surgical microscope comprising:

a contactless visualization system having an ophthalmic loupe and a wall;

said ophthalmic loupe configured to be positionable in front of a patient's eye and to supply a real and vertically and laterally inverted image of an eye fundus of the patient's eye in an intermediate image plane that is observable by the surgical microscope;

said ophthalmic loupe including a first lens element and a second lens element, wherein, in a state positioned in front of the patient's eye, said first lens element is closer to the patient's eye than said second lens element;

said wall extending from said first lens element to said second lens element, said wall having a free end in a form of a mount in which said second lens element is held; and, said mount including at least one cutout in which an edge of said second lens element is exposed in order to give a surgeon operating space.

* * * * *